United States Patent [19]
Deitermann et al.

[11] Patent Number: 5,891,386
[45] Date of Patent: Apr. 6, 1999

[54] METHOD FOR MAKING CATHETER BALLOONS

[75] Inventors: Morris H. Deitermann, San Diego; Don H. Tran, Westminster; Donald R. Waller, San Diego; David B. Cowgill, San Marcos, all of Calif.

[73] Assignee: Medtronic, Inc., Minneapolis, Minn.

[21] Appl. No.: 843,110

[22] Filed: Apr. 25, 1997

[51] Int. Cl.$^6$ .................................................. B29C 49/08
[52] U.S. Cl. .................... 264/526; 264/523; 264/532; 264/573; 604/96; 606/194
[58] Field of Search .................... 264/523, 529, 264/530, 532, 573, 526; 604/96; 606/194

[56] References Cited

U.S. PATENT DOCUMENTS

| | | | |
|---|---|---|---|
| 3,438,375 | 4/1969 | Ericson | 128/349 |
| 4,195,637 | 4/1980 | Grüntzig et al. | 128/348 |
| 4,637,396 | 1/1987 | Cook | 128/344 |
| 4,706,670 | 11/1987 | Andersen et al. | 128/344 |
| 4,762,130 | 8/1988 | Fogarty et al. | 128/348 |
| 5,295,959 | 3/1994 | Gurbel et al. | 604/96 |
| 5,308,356 | 5/1994 | Blackshear, Jr. et al. | 606/194 |
| 5,484,411 | 1/1996 | Inderbitzen et al. | 604/96 |
| 5,735,816 | 4/1998 | Lieber et al. | 604/96 |
| 5,749,852 | 5/1998 | Schwab et al. | 604/96 |

OTHER PUBLICATIONS

Porstmann, W.; *Ein neuer Korset–Ballonkatheter zur transluminalen Rekanalisation nach Dotter unter besonderer Berücksichtigung von Obliterationen an den Beckenarterien*, pp. 239–244.

*Primary Examiner*—Catherine Timm
*Attorney, Agent, or Firm*—Dianne Plunkett Latham; John R. Duncan; Harold R. Patton

[57] ABSTRACT

A method and apparatus for forming perfusion balloons from thermoplastic materials. A helical member having a cross section corresponding to a desired perfusion channel cross section is placed in a tubular mold in contact with the mold wall. A thermoplastic tube is inserted into the helical member in the mold. The assembly is heated to the glass transition temperature of the tube and the tube is pressurized to expand into contact with the helical member and mold wall. After cooling, the formed balloon is removed from the mold. The helical member has a "T" shaped, or rectangular, or square, or triangular cross section. Limited pre-pressure and pre-stretch are preferably applied prior to the tube expansion and post forming tube conditioning may be used. Axial stretching of the tube in a mold, with our without the helical member, by microprocessor controlled air actuators provides highest quality balloons having selected wall thicknesses.

18 Claims, 4 Drawing Sheets

METHOD FOR MAKING CATHETER BALLOONS

FIELD OF THE INVENTION

This invention relates to methods and apparatus for manufacturing perfusion dilatation catheter balloons for use in angioplasty and the like.

BACKGROUND OF THE INVENTION

Dilatation balloon catheters are well known and used regularly for coronary angioplasty procedures and other similar procedures. Atheromatous plaque adhering to a blood vessel wall and restricting blood flow therethrough is compressed against the vessel wall by a balloon that is positioned in the vessel at the plaque location. This dilates the vessel lumen to permit increased blood flow.

A typical balloon catheter includes two lengthwise lumens or channels, one for inflation of an inflatable balloon sealed to the distal catheter end and the other for insertion of a guidewire extending through the catheter to aid in positioning the catheter during use.

Many catheters have been designed for particular uses, having a variety of configurations, methods of construction and methods of use. Most have a generally tubular balloon that, when inflated, temporarily cuts off blood flow through the vessel. Serious consequences can occur when blood flow is stopped for an extended period. Therefore, inflation duration is generally relatively short, typically no more than 150–180 seconds. Longer inflation periods would be very desirable, since better plaque compression could be accomplished. Also, some patients cannot tolerate even short time blood occlusion in some vessels.

Attempts have been made to develop balloon configurations that will permit at least some continued blood flow during plaque compression. For example, catheters having an additional lumen have been used, with openings between the catheter exterior and the added lumen at both ends of the balloon, so that limited blood flow can bypass the balloon occlusion. However, this arrangement has had limited success, since only a very limited amount of blood can flow though the lumen and adding the lumen increases the diameter of the catheter, which itself will tend to retard blood flow. Thus, at most this arrangement will allow a very slightly longer balloon inflation period.

Blackshear et al. in U.S. Pat. No. 5,308,356 and others have disclosed catheter balloons with a spiral or corkscrew-like configuration when expanded. Such perfusion balloon catheters are intended to allow blood to flow in a spiral channel path past the balloon during balloon inflation. However, in practice, little if any blood flow is found to occur with these spiral balloons, apparently due to blockage of the balloon channels by the arterial intima or lining. Other spiral balloons have been used for other purposes, such as the Fogarty et al. arrangement described in U.S. Pat. No. 4,762,130 for embolectomy.

In attempting to overcome these channel blockage problems, generally tubular sheaths have been provided over the spiral balloon, as disclosed by Gurbel et al. in U.S. Pat. No. 5,295,959 and by Cordis in U.S. Pat. No. 5,484,411. These sheaths cover the outer portions of the balloon spiral lobe and resist entry of arterial intima into the spiral channels when the balloon is inflated. While often effective in increasing blood flow past the balloon, these sheaths are typically unbonded or only bonded by heat or adhesive to narrow lines along the balloon spiral and may come loose in use in a blood vessel, to the serious detriment of the patient. Further, "tenting" also occurs in the middle channels of a spiral balloon, with the sheath tending to fold into the channel, where the sheath is not bonded to the spiral under tension.

Such sheaths are also difficult to manufacture in a manner that will resist tearing of sheath end edges when in use and when being moved along a vessel to the desired location. Ends of the sheath that are located at narrower balloon end regions may result in the sheath ends folding or "tenting" into the spiral channels, decreasing blood flow. Any tears at the sheath ends will aggravate this channel blocking tendency.

A spiral wire may be contained within a spiral channel along the surface of a balloon to prevent the channel from stretching sufficiently to significantly decrease the channel cross section and severely reduce perfusion. While the spiral wire is generally effective in preventing channel expansion, the wire occupies space best used for perfusion. Also, the wire makes the balloon stiffer, interfering with tracking and making reaching a lesion more difficult. The balloon profile will be larger and rewrap will be more difficult.

Therefore, there is a continuing need for improvements in perfusion dilatation catheters manufacturing apparatus and methods of improved manufacturing efficiency and simplicity that provide improved balloon geometry, catheters that permit increased blood flow past the inflated balloon while maintaining the desired dilatation effect with respect to plaque or the like, that form perfusion channels having improved resistance to channel blockage, that allow improved tracking during insertion, and provide a smaller profile and improved rewrap.

SUMMARY OF THE INVENTION

The above-noted problems, and others, are overcome in accordance with this invention by a method and apparatus for forming perfusion balloon catheters in which a helical channel forming member is inserted into a tubular mold having a predetermined inside diameter corresponding to the outside diameter of the balloon to be formed, a tube of non-compliant thermoplastic material is inserted into the mold within the helical forming member, the thermoplastic material is heated to a temperature above its glass transition temperature, the tubing is pressurized to expand the tubing into contact with the helical forming member and the wall of the tubular mold, the tubing is cooled and the resulting formed tube having a helical channel is removed from the mold.

Preferably, a small initial gas pressure is applied to the tubing prior to heating to prevent the tubing from collapsing prior to the pressurization expansion step. While any suitable pressure may be used, generally best results are obtained with gas pressures in the 5 to 10 psi range.

A small stretch force is preferably applied to the tubing prior to the heating and expansion step so as to prevent the tubing from sagging into contact with the mold, which would cause uneven heating. For best results, this stretch force should be in the 0.05 to 0.15 lb. range.

Once the tubing has reached its glass transition temperature, the axial stretch force and the internal gas pressure are significantly increased. This causes the tubing to stretch rapidly as the forming pressure is applied to the tubing. As the tubing expands against the mold and forming member, the desired axial and radial orientation will be achieved, giving the balloon increased strength. Preferably, the axial stretch force and the gas pressure are applied independent of each other, so that each can be optimized in degree and timing for optimum results with different materials.

Once forming of the balloon is complete, the temperature of the mold is preferably increased to from about 190° to 300° F. for from about 10 to 12 seconds to condition the balloon material.

After completion of the conditioning step, the balloon is cooled to a temperature below about 100° F. For best results, cooling is accomplished at an average rate of at least about 4° F./second, because fast cooling preserves mechanical strength of the balloon and shortens the machine cycle time.

Once cooled, the internal gas pressure is released and the tubing is released from the gas pressurization fittings. An end of the mold is opened and the formed balloon with the helical channel forming member are removed together. If desired, a vacuum may be applied to the balloon, partially collapsing the balloon, to aid in removal from the mold. The forming member is then removed and the balloon is inflated to remove wrinkles. The resulting balloon may be used in any suitable perfusion balloon catheter apparatus and method.

This method may be performed under manual control of the various heating, cooling, pressurization, stretching, etc. functions, if desired. Optimally, the process will be controlled by a suitably programmed microprocessor control system that makes controlling and adjusting these various parameters convenient and accurate.

It is, therefore, an object of this invention to provide a method and apparatus for manufacturing a perfusion balloon having a helical channel of optimum cross section. Another object is to provide a perfusion balloon manufacturing method and apparatus that is less labor intensive, less likely to damage balloons during manufacture and with precise control over balloon geometry. A further object is to provide a perfusion balloon manufacturing method and apparatus that produces balloons having fewer parts, a lower balloon profile, improved rewrap characteristics and greater flexibility. Yet another object is to provide a perfusion balloon manufacturing method and apparatus capable of producing unobstructed helical channels having a wide variety of cross sectional shapes.

BRIEF DESCRIPTION OF THE DRAWING

Details of the invention, and of preferred embodiments thereof, will be further understood upon reference to the drawing, wherein:

FIG. 4 is a partially cut away elevation view of a perfusion balloon made using the helical member of FIGS. 2 and 3a;

DETAILED DESCRIPTION OF PREFERRED EMBODIMENTS

Figure 1:
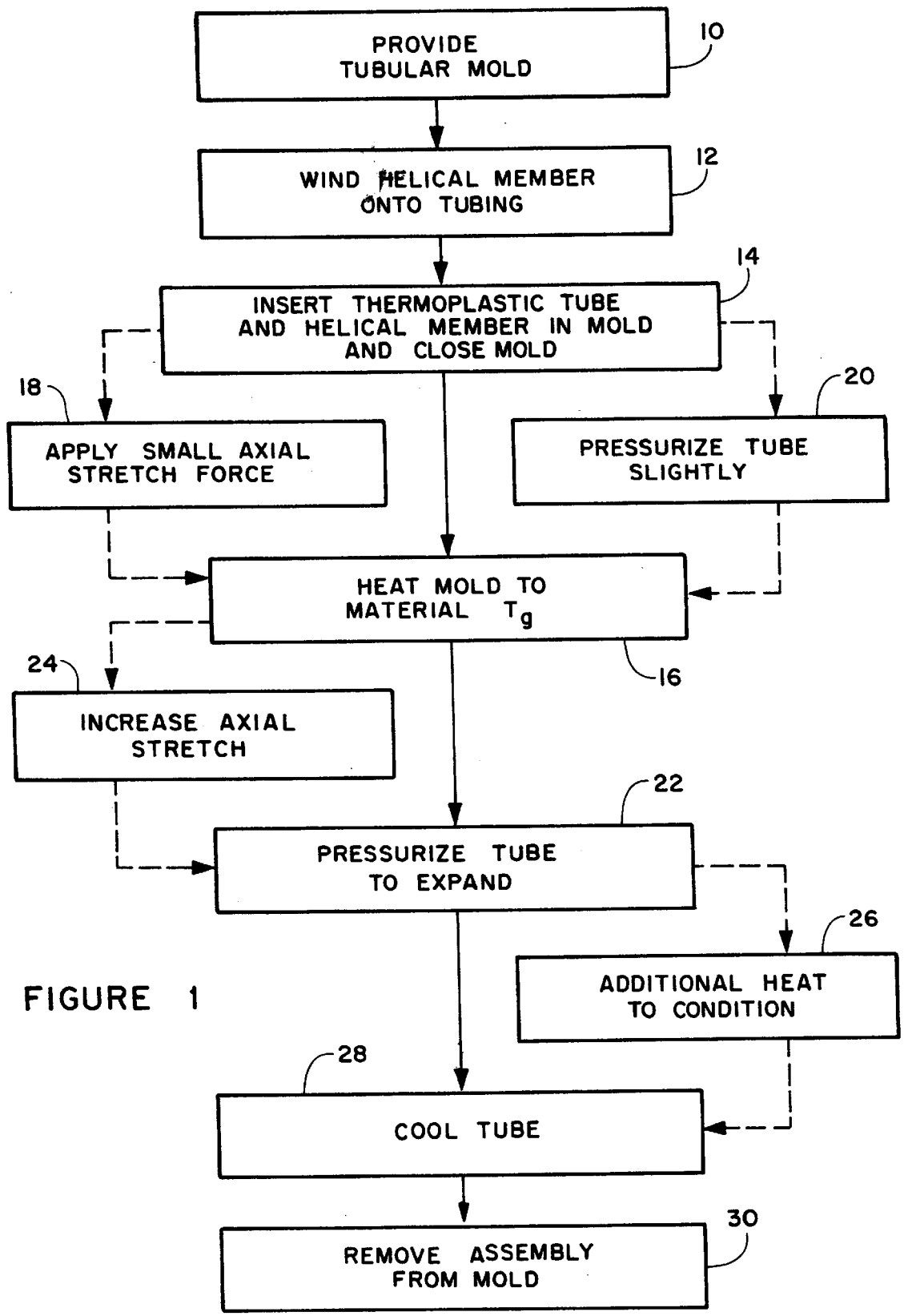
FIG. 1 is a schematic flow diagram of the perfusion balloon manufacturing method of this invention.

Referring to FIG. 1, there is seen a schematic block diagram of the method of this invention. Both the basic method and several preferred options are described.

Initially, a tubular mold is provided as indicated in block 10. Any suitable material may be used in this mold, which will have suitable dimensions consistent with the perfusion balloon to be formed. Typically, the mold will be formed by conventional machining techniques from a suitable material, such as stainless steel, copper, aluminum or glass, and will have a diameter of from about 0.078 to 0.2 in. and a length of from about 0.78 to 2.4 in. Preferably, the middle section of the mold containing the helical member is a copper alloy, which prevents damage and wear to the helical member.

A helical member having a shape corresponding to the desired perfusion channel is then inserted in the mold, block 12. Any suitable helical member cross sectional shape may be used. Typically, the cross section could be rounded, square, triangular, rectangular or any other desired shape to produce a perfusion channel having the desired characteristics. Square helical members are preferred for perfusion balloons as it permits greater fluid perfusion and results in a lower profile. A rectangular shape with the wider balloon surface side in contact with the vessel is preferable for dilatation purposes because it results in greater balloon surface area contact with the vessel.

The outside diameter of the helix will preferably be a tight slip fit with a clearance of about 0.001 within the mold. Any suitable cross section through the member may be used, as detailed below. Typically, the helical member will have, depending on the balloon diameter, a radial depth of from about 0.037 to 0.068 in., a width transverse to the radial depth of from about 0.010 to 0.10 in. and a pitch of from about 0.263 to 0.158 in.

A thermoplastic tube is then inserted into the helical member, block 14, to form the perfusion balloon. Any suitable thermoplastic material may be used. The material should have a burst rating of about 14 to 20 ATM and be thin and sufficiently flexible to wrap down to a small profile during rewrap when the balloon is deflated. Typical balloon materials include polyethylene, polyethylene terephthalate, polyamides, and mixtures thereof. Any suitable biaxially oriented material may be used, such as a blend of polyethylene terephthalate and an ethylene vinyl acetate copolymer as described in commonly owned copending U.S. Pat. No. 5,827,225, the disclosure of which is hereby incorporated by reference.

The mold is then heated to the glass transition temperature of the balloon material, block 16, by any suitable heating arrangement, such as resistance heaters, preferably at a heating rate of about 4° F. per second or faster.

Just prior to, or during initial heating, for best results a small axial stretch force is applied to the tubing, block 18. This prevents the tubing from sagging, which could cause the tubing to contact the mold and cause uneven heating. Preferably, the stretch force is from about 0.05 to 0.15 lbs. Also, it is generally desirable to apply a small amount of internal pressure to the tube, block 20, just before heating or during the initial heating, to prevent collapse of the tubing prior to balloon forming. Preferably, this initial pressure is from about 5 to 10 psi. While any suitable pressurizing gas may be used, nitrogen is generally preferred because it is clean, inexpensive, readily available in very high pressures and is non-oxidizing and non-toxic.

Once the material has reached its glass transition temperature, gas pressure is increased to the forming pressure, block 22. The optimum pressure will vary somewhat in accordance with the tubing material being used, but will generally be in the 100 to 350 psi range.

In order to provide optimum tube strength, the tubing axial stretch force is increased, block 24, when the temperature has reached approximately the material glass transition temperature. While the optimum stretch force applied will vary with the tubing material being used, generally that force will be in the 1 to 5 lb. range. The gas pressure and the axial stretch forces are preferably controlled and applied separately, since with different materials the optimum timing of the axial and radial stretching may be different with different materials.

Once tube expansion is complete, the tubing is preferably heated to a higher temperature to condition the balloon, block 26. Gas and stretch pressures are maintained during conditioning.

Once expansion (and conditioning, if used) is complete, the mold is cooled to approximately room temperature, block 28. For best results, cooling is rapid, preferably about at an average rate of about 4° F./second. The initial cooling rate can be higher, and decrease as room temperature is approached. This rapid cooling is beneficial to preserve the mechanical properties of the balloon material.

Finally, gas pressure is released, the mold gas-admitting fixtures and mold end fitting are released and the balloon having a helical perfusion channel corresponding to the helical member configuration is removed from the mold, block 30. In some cases, it is desirable to apply a slight vacuum, typically 27 to 28 in Hg, to the balloon to aid in removal of the balloon from the mold and helical member. Once the balloon is removed, it may be inflated at low pressure to remove wrinkles prior to assembly onto a catheter and wrapping for use.

Figure 2:
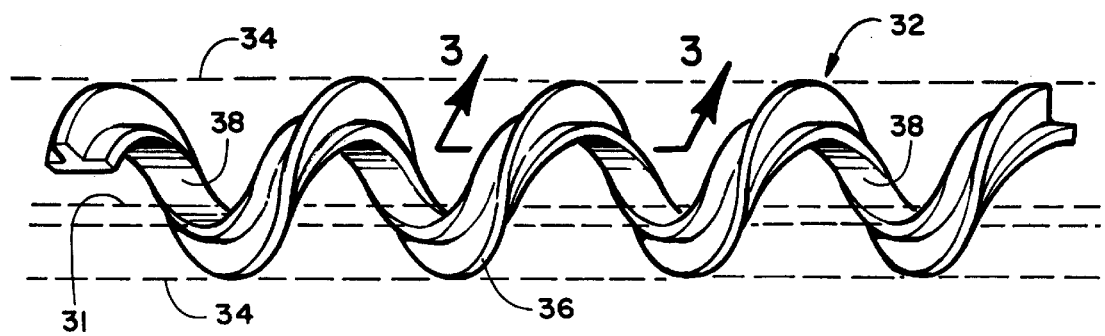
FIG. 2 is an elevation view of a helical channel forming wire useful in the method and apparatus of this invention.
Figures 3A, 3B, 3C:
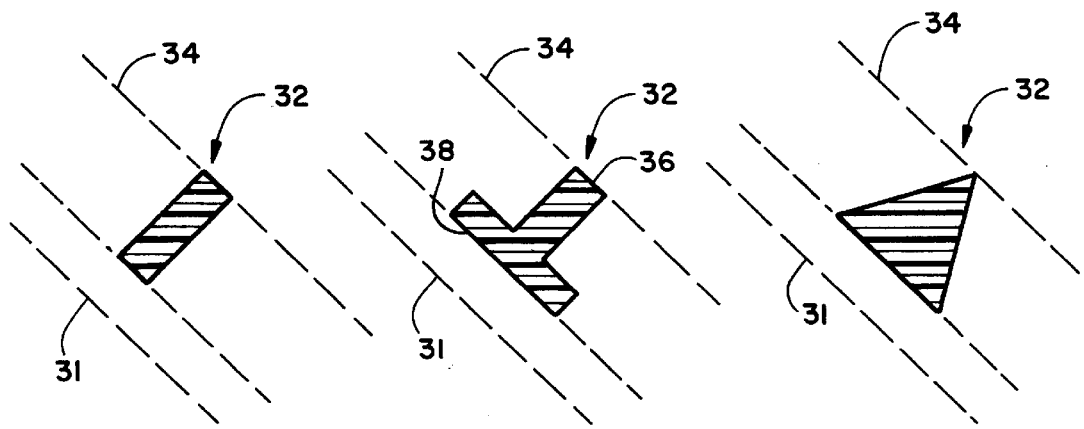
FIG. 3a is a section view taken on line 3—3 in FIG. 2.
FIGS. 3b–3d are section views taken on a line corresponding to line 3—3 in FIG. 2 for helical members having different cross sections.

FIGS. 2 and 3a–3c show several preferred helical member geometry's for use in the method described above. As seen in FIGS. 2 and 3a helical member 32 has a generally "T" shaped cross section, with narrow end or leg 36 of the "T" cross section extending outwardly. In a tubular mold, schematically indicated by broken lines 34, the end of leg 36 will contact the inner wall of the mold and the leg will lie generally on a radial line with the cross piece of the "T against the tubular preform 31 shown in broken lines. The top or cross piece 38 of the "T" cross section will lie transverse to such a radial line drawn from the centerline of the mold. Tube 31 is heated and expanded under high internal pressure to expand around member 36 and form a balloon as seen in FIG. 4.

This general configuration of helical member 32 provides a channel having a substantially enclosed volume for perfusion, with a small outer gap to resist entrance of arterial wall material into the channel. Helical member 32 may be formed from any suitable material. Typical materials include high strength, stiff synthetic resins, metals such as stainless steel, etc. The synthetic resin helical members can be conveniently formed by molding or casting processes while conventional machining processes are used with metals. A sheath tube may be provided over the exterior of balloon, as shown in FIG. 5b.

Figure 3D:
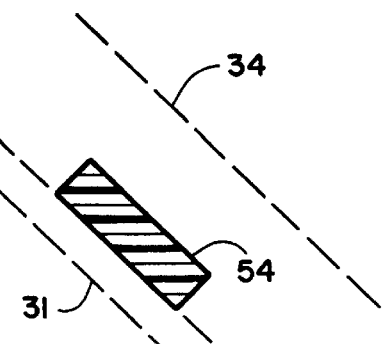

Three other preferred configurations for the helical member are shown in FIGS. 3b, 3c and 3d. As seen in FIG. 3b, helical member 32 may have an outwardly extending rectangular cross section. A member 32 with a triangular cross section is shown in FIG. 5c.

Figure 4:
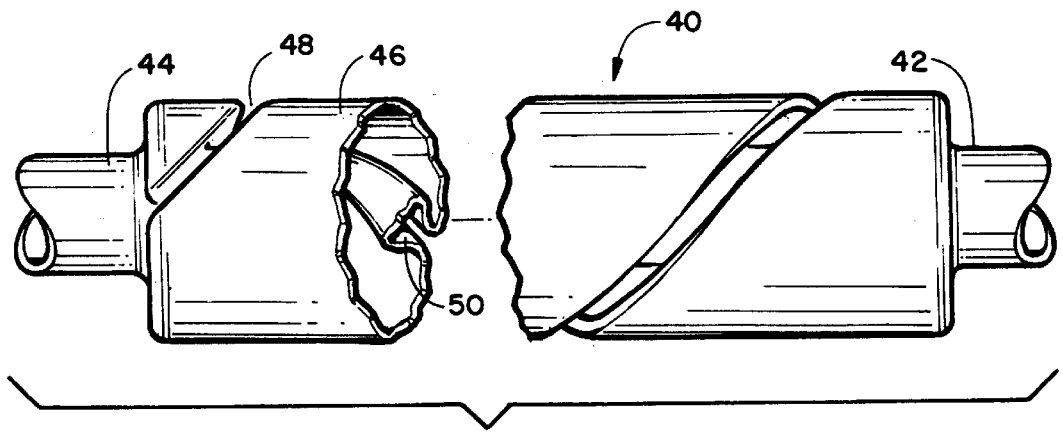
Figure 5A:
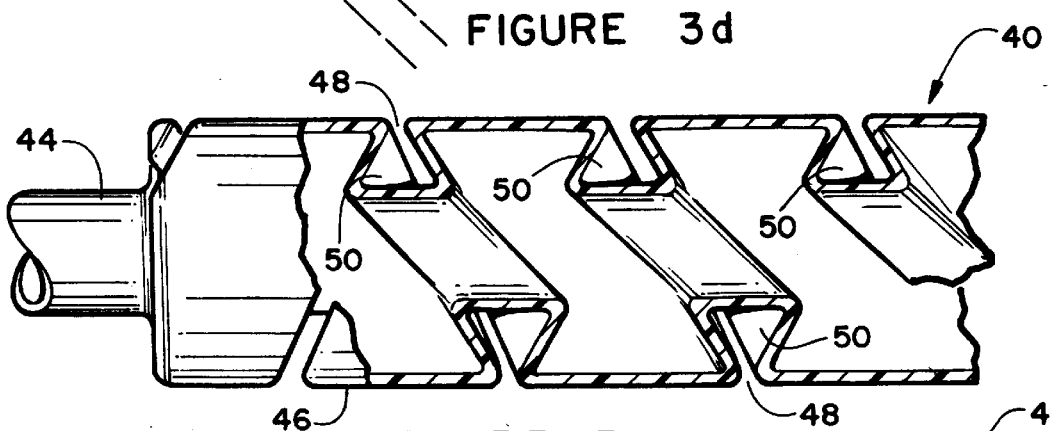
FIG. 5a–5c are partially cut away elevation view of balloons made using the helical members of FIGS. 3c, 3b and 3d, respectively.

A perfusion balloon 40 is schematically illustrated in FIGS. 4 and 5a. This balloon 40 was made by the above described method, using a helical member 32 having a cross section of the sort shown in FIGS. 3a or 3c. Balloon 40 includes narrow end sections 42 and 44, typically having approximately the original diameter of the unexpanded tube preform and an expanded center section 46. With the "T" cross section helical member 32, as seen in FIG. 2 and 3a or the triangular cross section seen in FIG. 3c, the outer line opening 48 into the perfusion channel 50 is narrow to resist having arterial material along the arterial wall pressed into the channel and blocking or limiting perfusion. At the same time, the actual channel 50 has a relatively large cross sectional area for maximum perfusion.

Figure 5B:
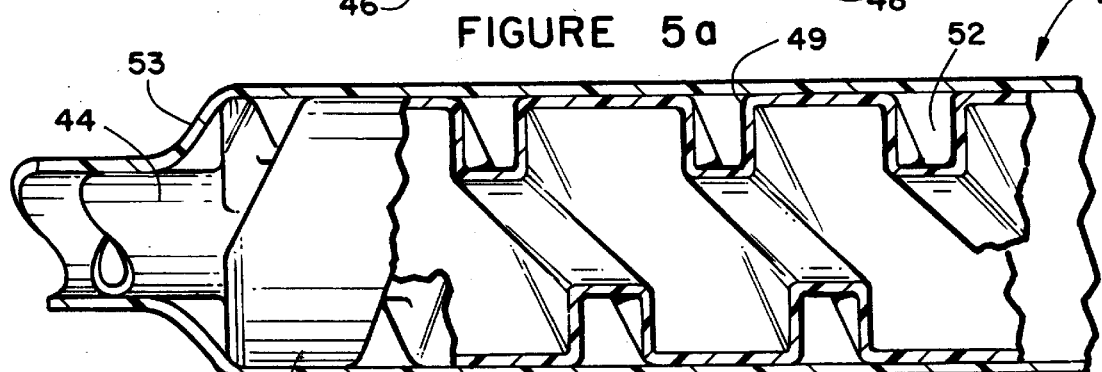
Figure 5C:
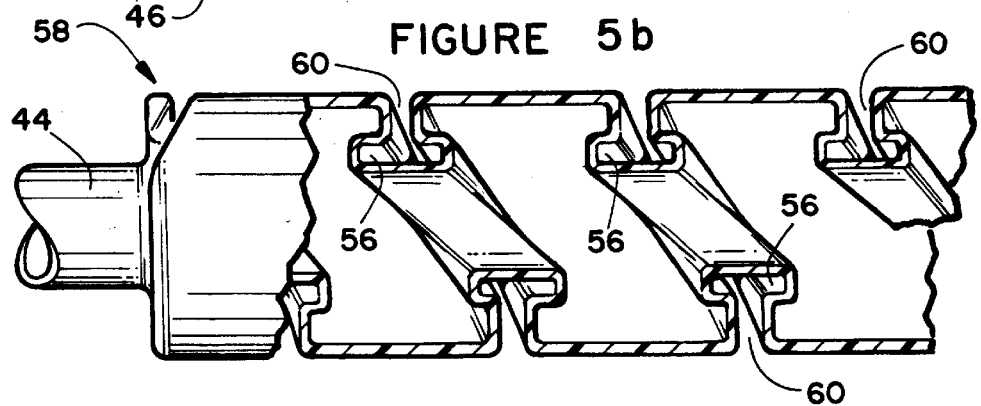

FIG. 5b shows an axial section view through a balloon 41 made with a forming member 32 having the cross section shown in FIG. 3b. Channels 52 thus have rectangular cross sections. Channels 52 could also be square or rectangular in the opposite direction. Since openings 49 into channels 52 are relatively wide, preferably a tubular sheath 53 is placed over balloon 41 to prevent foreign matter entering into the channels.

As seen in FIG. 3d, a narrow forming member 54 may be helically wound around tubular preform 31, spaced from the inner wall 34 of the mold. When expanded, a channel 56 is formed as seen in the axial section view through completed balloon 58 in FIG. 5c. The size of openings 60 will depend upon the balloon expansion pressure. With relatively low pressure, openings 60 will have a greater width. With relatively high pressure, the balloon material will wrap around the forming member 54 to the point where the opening is closed. In that case, if desired, an adhesive may be used to bond the abutting portions of the balloon that close opening 60. The result is an entirely submerged channel 56.

Figure 6:
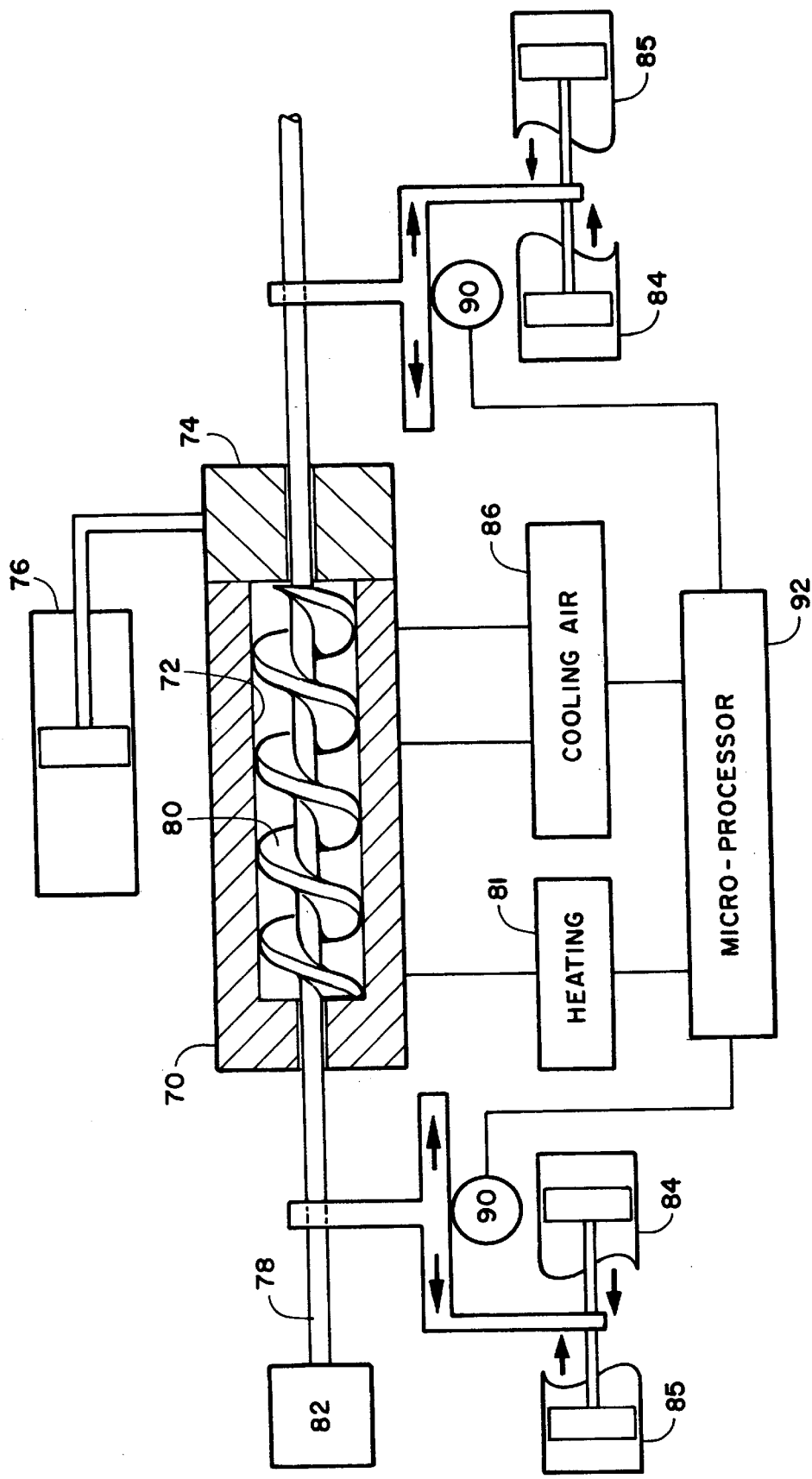
FIG. 6 is a schematic diagram of the apparatus of this invention.

A schematic block representation of the balloon forming apparatus is shown in FIG. 6. Mold 70 has a generally cylindrical central cavity 72 and an end cover opened and closed by an air actuator 76. A plastic tube 78 is wound or inserted into helical forming member 80 and the assembly is inserted into mold 70. Distal section 74 is then closed. A resistance heater 81 begins to heat mold 70 as the appropriate pressure is applied within tube 78 from pressurized gas source 82 to inflate the tube within the mold to form a balloon against helical member 80 and cavity 72. Stretch is applied to tube 78 during forming by air actuators 84. Stretch velocity and timing may be varied to produce any desired wall thickness characteristics. When forming is complete, mold 70 is air cooled from cool air source 86 and air pressure from pressurized air source 82 is reduced, return actuators 85 reduce the stretch and heater 81 is turned off, all in a predetermined sequence under control of a conventional microprocessor 92, which receives stretch information from encoders 90 and each of the other components and directs operation of those components.

Any suitable air actuators may be used for stretch actuators 84 and return actuators 85, such as the air powered actuators available from Airpot Corporation, Norwalk, Conn. Such air actuators are highly desirable because of the glass and carbon construction to eliminate friction in the air cylinder where stretching is performed by a slide. Motor driven actuators are undesirable since use speed and distance to determine the degree and rate of stretch, resulting in a lower level of precision and friction results from the moving mechanical parts. The greater precision of air actuators produces walls of more uniform thickness with fewer imperfections and, therefore, greater burst strength, typically one atmosphere greater burst strength than with mechanical actuators, and higher yields. This process produces better timing and easier implementation because less programming is required. The autoperfusion balloons are fully formed and squared as necessary.

With microprocessor control, velocity may be varied during forming, in accordance with predetermined set points and dynamic pressure changes to produce sections of differing balloon wall thickness. For example, thinner walls could be provided at either end of the balloon in the balloon cones to improve rewrap characteristics when stiffer balloon materials are used.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

We claim:

1. A method of forming perfusion balloons which comprises the steps of:
   providing a tubular mold having an internal mold wall and having a predetermined diameter corresponding to the diameter of balloon to be formed;
   inserting a tube comprising a thermoplastic material into a helical channel forming member;
   inserting said helical channel forming member with said tube inserted therein into said tubular mold;
   heating at least said tube to the glass transition temperature of said thermoplastic material;
   pressurizing said tube to expand said tube into contact with said helical member and said mold wall to form a balloon having a helical perfusion channel;
   cooling said tube to approximately room temperature; and
   removing said tube from said tubular mold and forming member.

2. The method of forming perfusion balloons according to claim 1 further including the step, prior to heating said tube, of pressurizing said tube up to about 5 to 10 psi and, after heating said tube to the balloon material glass transition temperature, increasing tube pressure to about 100 to 350 psi.

3. The method of forming perfusion balloons according to claim 1 further including the step of applying, prior to heating said tube, an axial stretch force of up to about 0.05 to 0.15 lb.

4. The method of forming perfusion balloons according to claim 1 further including the step, after said tube has been heated to its glass transition temperature, of applying an axial stretch force of from about 5 to 10 lb. to said tube to rapidly stretch and strengthen said tube.

5. The method of forming perfusion balloons according to claim 1 further including the step, after said cooling step, of applying a vacuum of from about 27–28 in Hg to aid removal of said tube.

6. The method of forming perfusion balloons according to claim 1 wherein said tube is formed from a material selected from the group consisting of polyethylene terephthalate, polyethylene, polyamide and mixtures thereof.

7. The method of forming perfusion balloons according to claim 1 wherein said helical forming member has a generally "T" shaped cross section having a leg and a top portion and is placed in said mold with the leg distal end extending along a radial line into contact with said mold wall and said top portion lying generally transverse to said radial line.

8. The method of forming perfusion balloons according to claim 1 wherein said helical forming member has a generally equilateral triangular cross section and is placed in said mold with a corner extending along a radial line into contact with said mold wall and a side approximately in contact with said tube.

9. The method of forming perfusion balloons according to claim 1 wherein said helical forming member has a generally rectangular cross section having two opposite shorter sides and two opposite longer sides and is placed in said mold with a said shorter extending along a radial line into contact with said mold wall and a said shorter side approximately in contact with said tube.

10. The method of forming perfusion balloons according to claim 1 wherein said helical forming member has a generally square cross section having two opposite sides of equal length and a second two opposite sides of equal length.

11. The method of forming perfusion balloons according to claim 1 wherein said helical forming member has a generally rectangular cross section having two opposite shorter sides and two opposite longer sides and is placed in said mold with a said longer side approximately in contact with said tube and a said longer side spaced from said mold wall.

12. The method of forming perfusion balloons according to claim 1 wherein said cooling is done at an average rate of at least about 4° F./sec.

13. A method of forming perfusion balloons which comprises the steps of:
   providing a tubular mold having an internal mold wall and having a predetermined diameter corresponding to the diameter of balloon to be formed;
   inserting a tube comprising a thermoplastic material into a channel forming member and inserting said channel forming member into said tubular mold with said tube therein
   heating at least said tube to the glass transition temperature of said thermoplastic material;
   axially stretching said tube;
   pressurizing said tube to expand said tube into contact with said mold wall to form a balloon;
   cooling said tube to approximately room temperature;
   releasing axial stretch; and
   removing said tube from said tubular mold.

14. The method according to claim 13 wherein said stretch is accomplished by connecting air actuators to both ends of said tube and causing said air actuators to move both ends away from each other.

15. The method according to claim 13 wherein said stretch force is from about 1 to 5 lb.

16. The method according to claim 13 further including applying an initial stretch force of from about 0.05 to 0.15 lb. prior to heating said tube.

17. The method according to claim 13 further including applying an internal pressure of from about 5 to 10 lb. to said tube prior to said heating.

18. The method according to claim 13 including varying stretching rate during stretch to vary balloon wall thickness.

* * * * *